(12) United States Patent
Abidin (10) Patent No.: US 9,980,758 B2
(45) Date of Patent: May 29, 2018

(54) MINIMALLY INVASIVE COUNTER-TORQUE WRENCH SYSTEM

(71) Applicant: Blackstone Medical, Inc., Lewisville, TX (US)

(72) Inventor: Cin K. Abidin, Lewisville, TX (US)

(73) Assignee: Blackstone Medical, Inc., Lewisville, TX (US)

( * ) Notice: Subject to any disclaimer, the term of this patent is extended or adjusted under 35 U.S.C. 154(b) by 256 days.

(21) Appl. No.: 14/092,154

(22) Filed: Nov. 27, 2013

(65) Prior Publication Data

US 2015/0148849 A1 May 28, 2015

(51) Int. Cl.
*A61B 17/88* (2006.01)
*A61B 17/70* (2006.01)
*A61B 17/00* (2006.01)

(52) U.S. Cl.
CPC .... *A61B 17/7091* (2013.01); *A61B 17/00234* (2013.01)

(58) Field of Classification Search
CPC ..... A61F 2002/4623; A61F 2002/4624; A61B 17/7076; A61B 17/7077; A61B 17/7082
USPC .......................... 606/86 R, 99, 279, 250–278
See application file for complete search history.

(56) References Cited

U.S. PATENT DOCUMENTS

| 920,188 | A | 5/1909 | Schumacher |
| 2,987,080 | A | 6/1961 | Chandler et al. |
| 3,477,486 | A | 11/1969 | Modrey |
| 5,505,732 | A | 4/1996 | Michelson |
| 5,797,911 | A | 8/1998 | Sherman et al. |
| 6,485,491 | B1 | 11/2002 | Farris et al. |
| 7,250,052 | B2 | 7/2007 | Landry et al. |
| 7,338,491 | B2 | 3/2008 | Baker et al. |
| 7,377,923 | B2 | 5/2008 | Purcell et al. |

(Continued)

FOREIGN PATENT DOCUMENTS

FR 2954689 A1 7/2011
WO 2011/133160 A1 10/2011

OTHER PUBLICATIONS

International Search Report and Written Opinion, PCT/US2012/049180, dated Oct. 26, 2012, 9 pages.

(Continued)

*Primary Examiner* — Eduardo C Robert
*Assistant Examiner* — Tara R Carter
(74) *Attorney, Agent, or Firm* — Baker & McKenzie LLP (57) ABSTRACT

A minimally invasive counter-torque system may comprise a bone screw system, a counter-torque wrench, a set screw driver, a counter-torque wrench handle, and a removable set screw driver handle. A body of the counter-torque wrench may be positioned entirely within a space as defined by or between removable arms of a tulip head of the bone screw system, such that only the wings of the counter-torque wrench extend beyond a width of the bone screw system. In operation, the counter-torque wrench handle may be received on a proximal end of the counter-torque wrench and may be used to stabilize and prevent rotation of the counter-torque wrench and the bone screw system. Then, the removable set screw drive handle may be engaged to a proximal end of the set screw driver and may be used to fasten a set screw into the saddle of the bone screw system.

10 Claims, 8 Drawing Sheets

(56) References Cited

U.S. PATENT DOCUMENTS

| | | | |
|---|---|---|---|
| 7,666,189 B2 * | 2/2010 | Gerber | A61B 17/7074 606/104 |
| 7,749,258 B2 | 7/2010 | Biedermann et al. | |
| 7,766,946 B2 | 8/2010 | Bailly | |
| 7,811,310 B2 | 10/2010 | Baker et al. | |
| 7,922,725 B2 | 4/2011 | Darst Rice et al. | |
| 7,942,909 B2 | 5/2011 | Hammill, Sr. et al. | |
| 7,951,173 B2 | 5/2011 | Hammill, Sr. et al. | |
| 8,066,745 B2 | 11/2011 | Kirschman | |
| 8,100,946 B2 | 1/2012 | Strausbaugh et al. | |
| 8,142,436 B2 | 3/2012 | Kirschman | |
| 8,167,910 B2 | 5/2012 | Nilsson | |
| 8,221,472 B2 | 7/2012 | Peterson et al. | |
| 8,419,778 B2 | 4/2013 | Barry | |
| 8,430,914 B2 | 4/2013 | Spratt et al. | |
| 8,882,817 B2 | 11/2014 | Jones et al. | |
| 8,951,290 B2 | 2/2015 | Hammer et al. | |
| 2002/0120275 A1 | 8/2002 | Schmieding et al. | |
| 2003/0105460 A1 | 6/2003 | Crandall et al. | |
| 2003/0231927 A1 | 12/2003 | Hale | |
| 2004/0176766 A1 | 9/2004 | Shluzas | |
| 2004/0186483 A1 | 9/2004 | Bagby | |
| 2004/0225289 A1 | 11/2004 | Biedermann et al. | |
| 2005/0043735 A1 | 2/2005 | Ahmad | |
| 2005/0131408 A1 * | 6/2005 | Sicvol | A61B 17/7032 606/86 A |
| 2006/0142762 A1 | 6/2006 | Michelson | |
| 2006/0200131 A1 | 9/2006 | Chao et al. | |
| 2007/0016200 A1 | 1/2007 | Jackson | |
| 2007/0078460 A1 | 4/2007 | Frigg et al. | |
| 2007/0118123 A1 | 5/2007 | Strausbaugh et al. | |
| 2007/0239159 A1 | 10/2007 | Altarac et al. | |
| 2007/0281274 A1 | 12/2007 | Schraffran et al. | |
| 2008/0009862 A1 | 1/2008 | Hoffman | |
| 2008/0051794 A1 * | 2/2008 | Dec | A61B 17/7091 606/250 |
| 2008/0125817 A1 * | 5/2008 | Arnett | A61B 17/7002 606/319 |
| 2008/0147129 A1 | 6/2008 | Biedermann et al. | |
| 2009/0076552 A1 | 3/2009 | Tornier | |
| 2009/0198280 A1 | 8/2009 | Spratt et al. | |
| 2009/0281550 A1 | 11/2009 | Keller | |
| 2009/0306721 A1 | 12/2009 | Kirschman | |
| 2010/0152785 A1 | 6/2010 | Forton et al. | |
| 2010/0212460 A1 | 8/2010 | Buss et al. | |
| 2010/0298891 A1 | 11/2010 | Jackson | |
| 2010/0305621 A1 | 12/2010 | Wang et al. | |
| 2010/0312288 A1 | 12/2010 | Hammill, Sr. et al. | |
| 2011/0046683 A1 | 2/2011 | Biedermann et al. | |
| 2011/0077694 A1 | 3/2011 | Biedermann et al. | |
| 2011/0152940 A1 | 6/2011 | Frigg et al. | |
| 2011/0160778 A1 | 6/2011 | Elsbury | |
| 2011/0172714 A1 | 7/2011 | Boachie-Adjei et al. | |
| 2011/0178559 A1 | 7/2011 | Barry | |
| 2011/0184469 A1 * | 7/2011 | Ballard | A61B 17/7091 606/279 |
| 2011/0263945 A1 * | 10/2011 | Peterson | A61B 17/7074 600/213 |
| 2011/0282399 A1 | 11/2011 | Jackson | |
| 2012/0031792 A1 | 2/2012 | Petit | |
| 2012/0046699 A1 | 2/2012 | Jones et al. | |
| 2013/0096624 A1 | 4/2013 | Di Lauro et al. | |
| 2013/0110176 A1 | 5/2013 | Rezach et al. | |
| 2013/0131734 A1 | 5/2013 | Longtain et al. | |
| 2013/0226243 A1 | 8/2013 | Kraus | |
| 2015/0272627 A1 | 10/2015 | Jackson | |

OTHER PUBLICATIONS

International Search Report and Written Opinion, PCT/US2014/061293, dated Jan. 23, 2015, 12 pages.

U.S. Office Action, U.S. Appl. No. 13/196,635, dated May 8, 2015, 28 pages.

U.S. Office Action, U.S. Appl. No. 14/037,011, dated Jun. 5, 2015, 30 pages.

U.S. Office Action, U.S. Appl. No. 14/059,203, dated May 18, 2015, 46 pages.

U.S. Office Action, U.S. Appl. No. 14/037,011, dated Apr. 21, 2016, 30 pages.

* cited by examiner

MINIMALLY INVASIVE COUNTER-TORQUE WRENCH SYSTEM

FIELD OF THE DISCLOSURE

The present disclosure relates to counter-torque wrenches and counter-torque wrench systems. More specifically, the present disclosure relates to minimally invasive counter-torque wrenches or counter-torque wrench systems that may be used with bone screw systems.

BACKGROUND OF THE DISCLOSURE

The spinal column of bones is a highly complex anatomical structure that includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction. The more than 20 discrete bones of an adult human spinal column are anatomically categorized as one of four classifications—cervical, thoracic, lumbar, or sacral—and are coupled together sequentially to one another by a tri-joint complex that consists of an anterior disc and two posterior facet joints. The anterior discs of adjacent bones are cushioned by cartilage spacers referred to as intervertebral discs or vertebrae. The cervical portion of the spine comprises the top of the spine up to the base of the skull and includes the first seven vertebrae. The intermediate 12 bones are thoracic vertebrae, and connect to the lower spine comprising the 5 lumbar vertebrae. The base of the spine comprises sacral bones, including the coccyx. With its complex nature, however, there is also an increased likelihood that surgery may be needed to correct one or more spinal pathologies.

Various systems exist for connecting fastener elements (e.g., pedicle screws) to bones for the purpose of vertebral fixation. Such systems may use a plurality of bone screws fitted in tulip heads where the tulip heads may be aligned using a mounting rod. Set screws may be disposed above the mounting rod and fastened against threads in saddles of the tulip heads. Such fastening may secure components within the saddle and provide overall stability to a bone screw system. In order to fasten a set screw, the set screw may need to be lowered through a channel or spacing between removable arms of the tulip head. Once lowered, a counter-torque wrench system may be used to reach the set screw at a distal end of the removable arms and then be used to fasten a set screw into the threads of the saddle.

For surgical proceedings, the size of incisions made in a patient may be dictated by the size or width of the components that need to be inserted into a patient's body and the size of the tools required to install such components. Accordingly, a need has arisen for an improved counter-torque wrench that advantageously provides a more minimally invasive system that allows for smaller incisions to be made during surgery. Therefore, a smaller, more minimally invasive counter torque wrench is desired.

SUMMARY

The present disclosure relates, according to some embodiments, to counter-torque wrenches and counter-torque wrench systems. A counter-torque wrench system may comprise a counter-torque wrench comprising a proximal end, a distal end, a body, at least one wing, and a hollow channel. The at least one wing may be disposed at a distal end of the counter-torque wrench. A hollow channel may extend from the proximal end to the distal end of the counter-torque wrench. A counter-torque wrench system may further comprise a set screw driver comprising a proximal end and a distal end. The distal end of the set screw driver may comprise an engaging member. The body of the counter-torque wrench may be operable to be received within a tulip head of a bone screw system. The set screw driver may be operable to be received within the hollow channel of the counter-torque wrench.

In some embodiments, a proximal end of a counter-torque wrench may comprise an annular protrusion. An annular protrusion may comprise at least one slot disposed at a distal end of the annular protrusion. The at least one slot may be operable to receive at least a distal portion of a removable arm of a tulip head.

A proximal end of a counter-torque wrench may be operable to removably engage with a counter-torque wrench handle.

A counter-torque wrench may comprise at least one wing. In some embodiments, a counter-torque wrench may comprise two wings. The at least one wing may comprise a curved surface at a distal end of the wing. The curved surface may be operable to bias against a curvature of a mounting rod of the bone screw system. The at least one wing may be disposed outside of the tulip head of a bone screw system.

In some embodiments, a body of a counter torque wrench may further comprise a plurality of indentations disposed along an axis as defined from the proximal end of the counter-torque wrench to the distal end of the counter-torque wrench. The plurality of indentations may be operable to be engaged with a compression tool.

A set screw driver of a counter-torque wrench system may be operable to rotate within a hollow channel of a counter-torque wrench. An engaging member of a set screw driver may be operable to mate with a set screw and may secure the set screw within a bone screw system. A proximal end of a set screw driver may be operable to engage with a T-handle.

According to some embodiments of the present disclosure, methods of securing a set screw within a bone screw system may be provided. A method may comprise providing a bone screw system, wherein the bone screw system may comprise a tulip head comprising a saddle and at least one removable arm. A method may further comprise disposing a set screw within a saddle, and inserting a counter-torque wrench into the tulip head. A counter-torque wrench may comprise a proximal end, a distal end, a body, at least one wing, and a hollow channel. The at least one wing may be disposed at a distal end of the counter-torque wrench. A hollow channel may extend from the proximal end to the distal end of the counter-torque wrench. A counter-torque wrench system may further comprise a set screw driver comprising a proximal end and a distal end. The distal end of the set screw driver may comprise an engaging member. A method may further comprise fastening the set screw into the saddle.

A method may further comprise securing at least a distal portion of a removable arm of a tulip head within a slot disposed at a distal end of an annular protrusion. A method may further comprise disposing on a proximal end of a counter-torque wrench a counter-torque wrench handle, and using a counter-torque wrench handle to maintain a rotational orientation of a counter-torque wrench. A method may further comprise biasing each of a curved surface against a curvature of a mounting rod of a bone screw system. A method may further comprise disposing an at least one wing outside of a tulip head of a bone screw system. A method may further comprise engaging any of a plurality of indentations on a body of a counter-torque wrench with a compression tool. A method may further comprise mating an engaging member with a set screw, and fastening a set screw into a saddle by rotating the set screw driver. A method may further comprise engaging a removable set screw driver handle to a proximal end of a set screw driver.

BRIEF DESCRIPTION OF THE DRAWINGS

Embodiments are illustrated by way of example in the accompanying figures, in which like reference numbers indicate similar parts, and in which.

DETAILED DESCRIPTION

The present disclosure relates to counter-torque wrenches and counter-torque wrench systems. More specifically, the present disclosure relates to minimally invasive counter-torque wrenches or counter-torque wrench systems that may be used with bone screw systems.

One of ordinary skill in the art would appreciate that a bone screw system may be connected or affixed within a patient's body. Thus, one of ordinary skill in the art would appreciate that, as used with respect to the components of the bone screw system, a proximal end or proximally refers to closer to the patient's body or directed towards the patient's body. In contrast, a distal end or distally, as used with respect to the components of the bone screw system, refers to further from the patient's body or directed away from the patient's body.

One of ordinary skill in the art would also appreciate that a counter-torque wrench system may be used or otherwise manipulated by a user (i.e., a surgeon). Thus, one of ordinary skill in the art would appreciate that, with respect to the components of the counter-torque wrench system, a proximal end or proximally refers to closer to the user's body or directed towards the user's body. In contrast, a distal end or distally, as used with respect to the components of the counter-torque wrench system, refers to further from the user's body or directed away from the user's body.

Bone screw systems may comprise tulip heads and bone screws. Bone screws, seated within a saddle of a tulip head, may be secured into a portion of a bone. In some systems, bone screws may be secured into a pedicle region of the spine. One or more tulip heads, with bone screws seated therein, may be stabilized by aligning a mounting rod through the tulip heads. A mounting rod may be secured within a saddle of the tulip head by use of a set screw. A set screw may be disposed at a distal end of the saddle. Disposing the set screw in the saddle may require or involve fastening threads of the set screw into or against corresponding threads on a distal end or top of the saddle. A fastened set screw may bias against a distal side of the mounting rod and exert pressure thereon, which may advantageously provide for a secure and stable bone screw system, and prevent undesired movement of components within the saddle of the bone screw system. Accordingly, it is desirable to provide for systems and/or methods of fastening a set screw into a saddle in a compact and secure manner that are minimally invasive to a patient.

Figure 1:
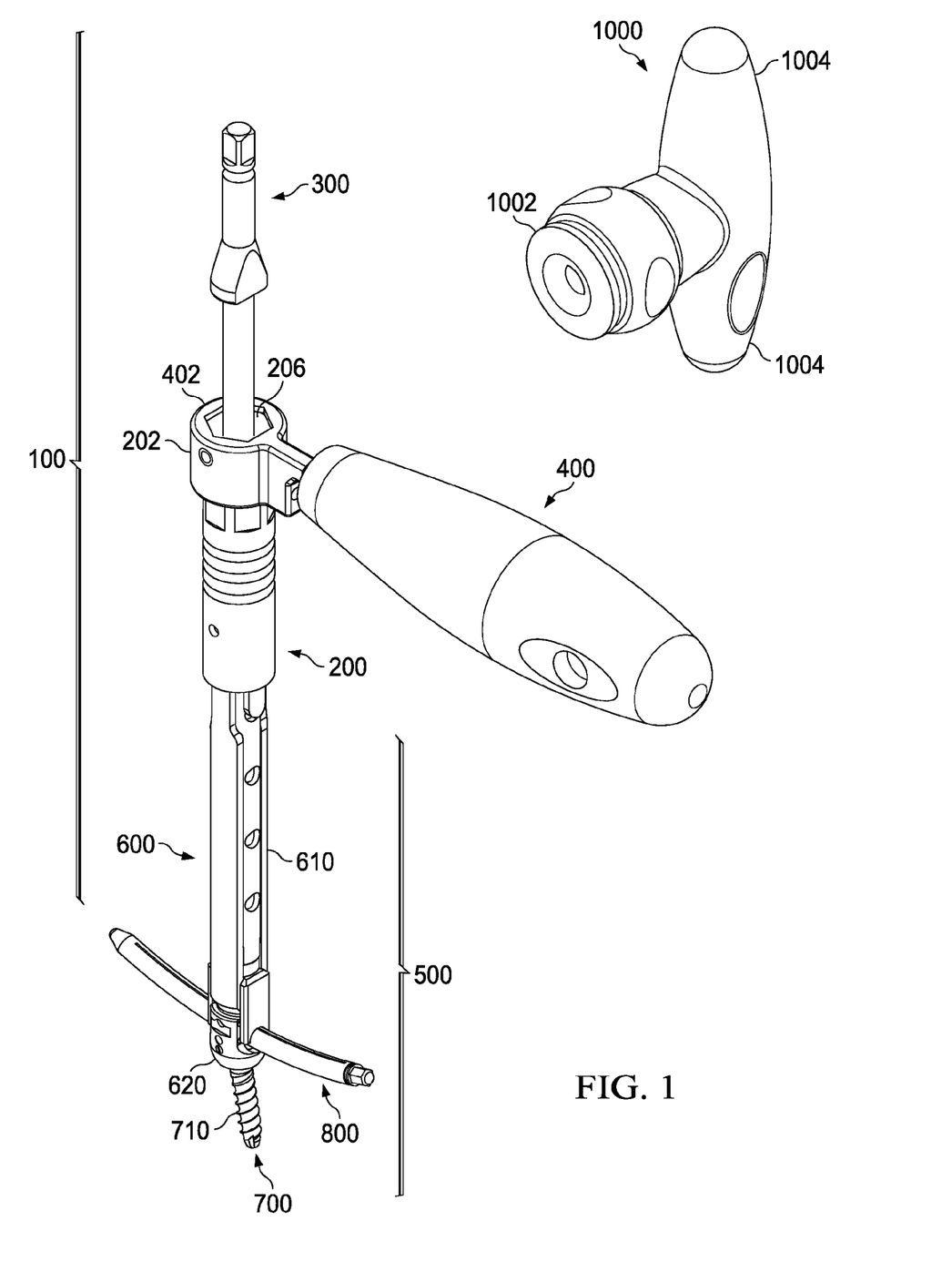
FIG. 1 illustrates a perspective view of a counter-torque wrench system according to one embodiment of the present disclosure.

FIG. 1 illustrates a perspective view of a counter-torque wrench system 100 according to one embodiment of the present disclosure. More specifically, FIG. 1 illustrates the counter-torque wrench system 100 engaged with a bone screw system 500.

As shown in FIG. 1, the counter-torque wrench system 100 may comprise a counter-torque wrench 200, a set screw driver 300, and a counter-torque wrench counter-torque wrench handle 400.

As shown in FIG. 1, the bone screw system 500 may comprise a tulip head 600, a bone screw 700, and a mounting rod 800. The tulip head 600 may comprise at least one removable arm 610 and a saddle 620. Some tulip heads 600 may comprise two removable arms 610, wherein each removable arm 610 extends distally from a proximal end of the saddle 620 of the tulip head 600, and wherein the removable arms 610 are spaced apart from one another to allow a set screw (not shown) to be received therebetween.

As shown in FIG. 1, the bone screw 700 may be seated within the saddle 620. A bone screw head of the bone screw 700 may rest or be seated within the saddle 620 while a bone connection element 710, comprising external threads, may extend proximally from a proximal cavity or aperture in the saddle 620. Thus, the bone screw head of the bone screw 700 may not be visible from the perspective view shown in FIG. 1. Similarly, the set screw may be disposed within the saddle 620 and above the mounting rod 800. Thus, the set screw may also not be visible from the perspective view of FIG. 1.

FIG. 1 illustrates the counter-torque wrench system 100 engaged with the bone screw system 500, which may comprise inserting the counter-torque wrench 200 into the tulip head 600. The counter-torque wrench handle 400 may be secured at a proximal end 202 of the counter-torque wrench 200. The set screw driver 300 may be inserted within a hollow channel 206 of the counter-torque wrench 200. The set screw driver 300 may be received within the hollow channel 206 and extend completely therethrough from the proximal end 202 of the counter-torque wrench 200 to a distal end of the counter-torque wrench 200. Thus, the set screw driver 300 may be operable to mate with the set screw disposed in the saddle 620 of the tulip head 600.

As seen in FIG. 1, the counter-torque wrench system 100 may further comprise a removable set screw driver handle 1000. The removable set screw driver handle 1000 may be engaged with or secured to the set screw driver 300 as a means of rotating or otherwise manipulating the set screw driver 300 and the set screw. In some embodiments, a proximal end of the set screw driver 300 may be operable to engage with the removable set screw driver handle 1000. The removable set screw driver handle 1000 may comprise an engagement portion 1002 and at least one counter-torque wrench handle end 1004.

Additional features and advantages of various embodiments of the counter-torque wrench system 100 of the present disclosure will become apparent to one of ordinary skill in the art having the benefit of the present disclosure.

Figure 2A:
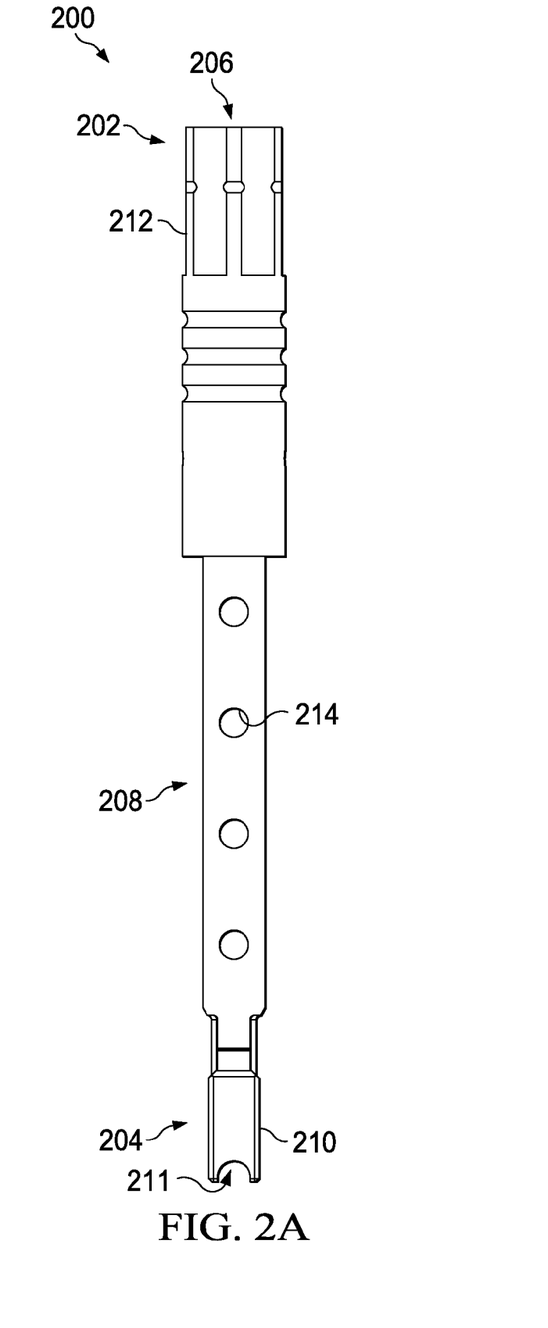
FIG. 2A illustrates a profile view of a counter-torque wrench according to one embodiment of the present disclosure.
Figure 2B:
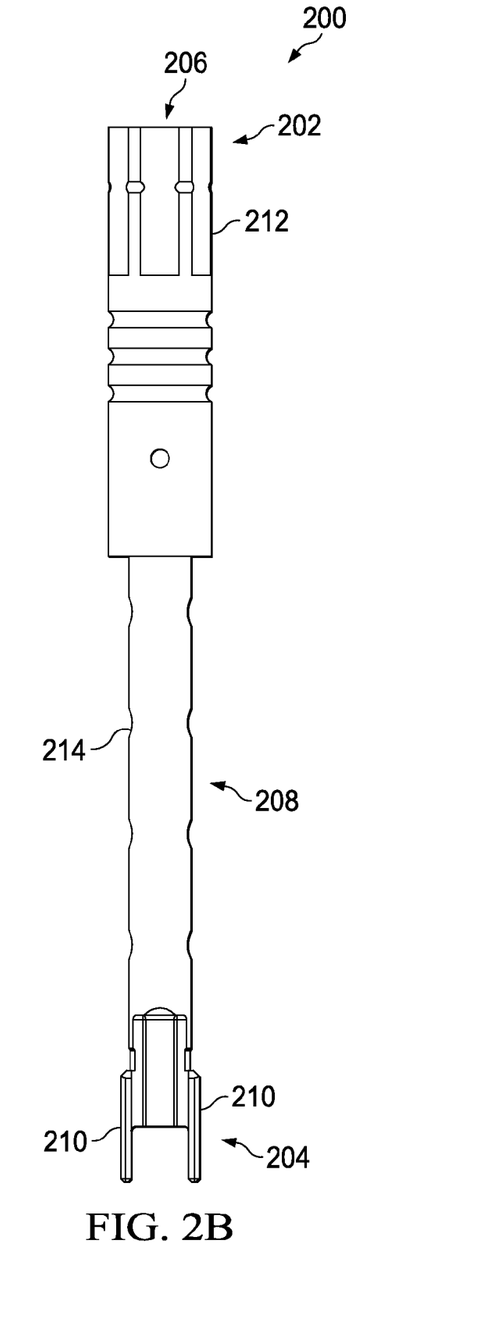
FIG. 2B illustrates another profile view of a counter-torque wrench according to one embodiment of the present disclosure.

FIG. 2A and FIG. 2B illustrate profile views of the counter-torque wrench 200 of FIG. 1, according to one embodiment of the present disclosure. FIG. 2A and FIG. 2B, by way of example, may depict the same counter-torque wrench 200 rotated 90 degrees about an axis defined from the proximal end 202 to a distal end 204. As shown in FIG. 2A and FIG. 2B, the counter-torque wrench 200 may comprise the proximal end 202, the distal end 204, a body 208, the hollow channel 206, and at least one wing 210.

The proximal end 202 may be operable to or be configured to engage with the counter-torque wrench handle 400 (as shown in FIG. 1) or otherwise allow for manipulation. Such manipulation, which may comprise rotation or repositioning of the counter-torque wrench 200 or may prevent rotation of the counter-torque wrench 200, may be performed by a surgeon during a surgical operation.

The distal end 204 may be operable to or be configured to engage with components of the bone screw system 500 (as shown in FIG. 1). For example, in some embodiments, a curved surface 211 of the wings 210 at the distal end 204 may be operable to engage with and bias against the mounting rod 800 of the bone screw system 500 (as shown in FIG. 1).

The body 208 of the counter-torque wrench 200 may comprise an elongated cylindrical structure extending from the proximal end 202 to the distal end 204. The body 208 may be operable to be received within the tulip head 600 of the bone screw system 500. The cylindrical shape or structure of the body 208 may advantageously promote insertion of the counter-torque wrench 200 into the tulip head 600 of the bone screw system 500. The cylindrical shape may provide for a curvature on the body 208 that may correspond with an interior curvature of the removable arms 610 of the tulip head 600 (as shown in FIG. 1). In some embodiments, the body 208 may be positioned entirely within a space as defined by or between the removable arms 610 of the tulip head 600.

The hollow channel 206 of the counter-torque wrench 200 may extend from the proximal end 202 to the distal end 204. The hollow channel 206 may be operable to receive the set screw driver 300 therein (as shown in FIG. 1).

The counter-torque wrench 200 may comprise the at least one wing 210. The at least one wing 210 may be disposed at the distal end 204 of the counter-torque wrench 200. As shown in FIG. 2A and FIG. 2B, in some embodiments, the counter-torque wrench 200 may comprise two wings 210. Each of the at least one wing 210 may comprise the curved surface 211 at a distal end of the wing 210.

In some embodiments, the counter-torque wrench 200 may further comprise an annular protrusion 212. In some embodiments, the counter-torque wrench 200 may further comprise a plurality of indentations 214.

Figure 3A:
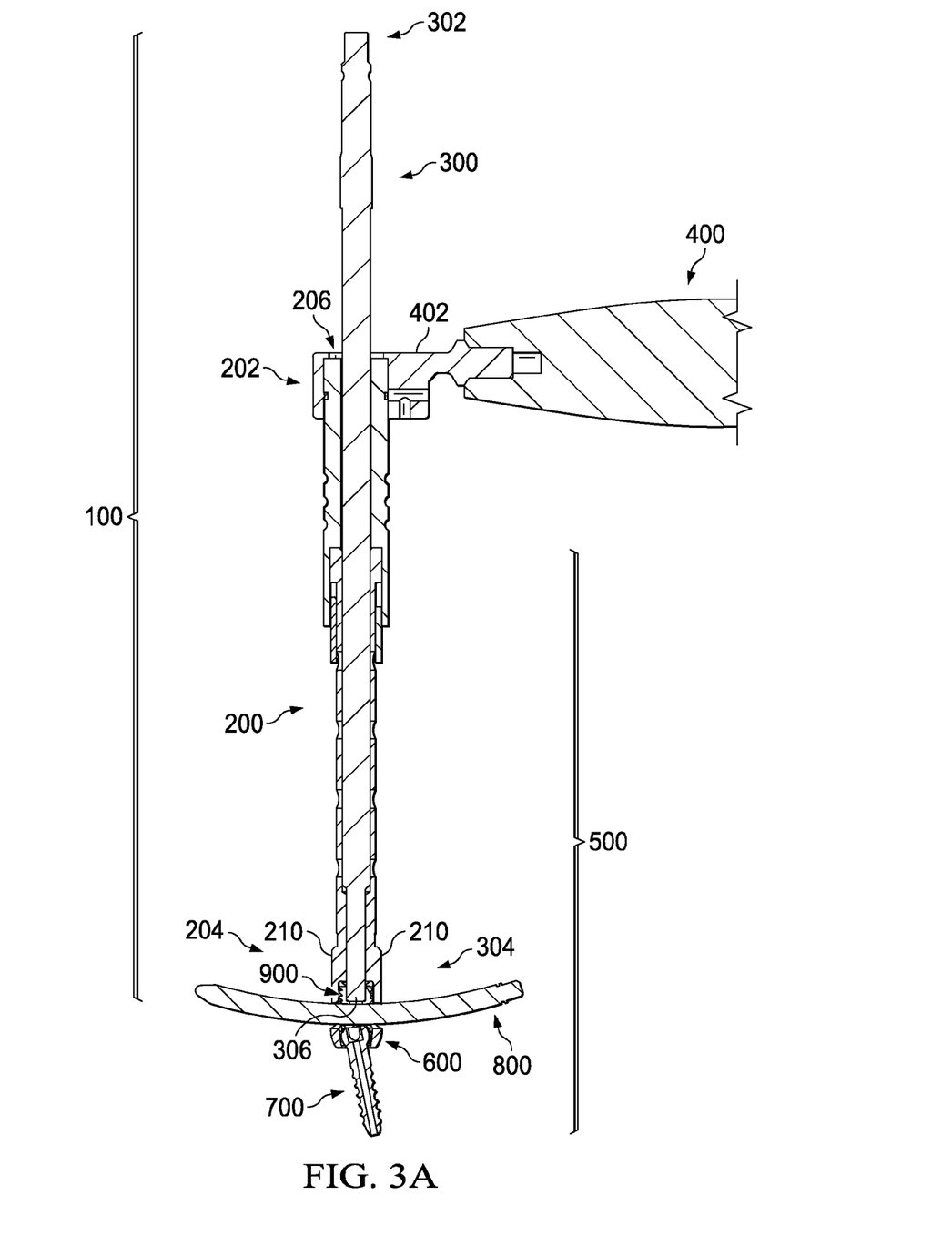
FIG. 3A illustrates a cross-sectional profile view of a counter-torque wrench system according to one embodiment of the present disclosure.
Figure 3B:
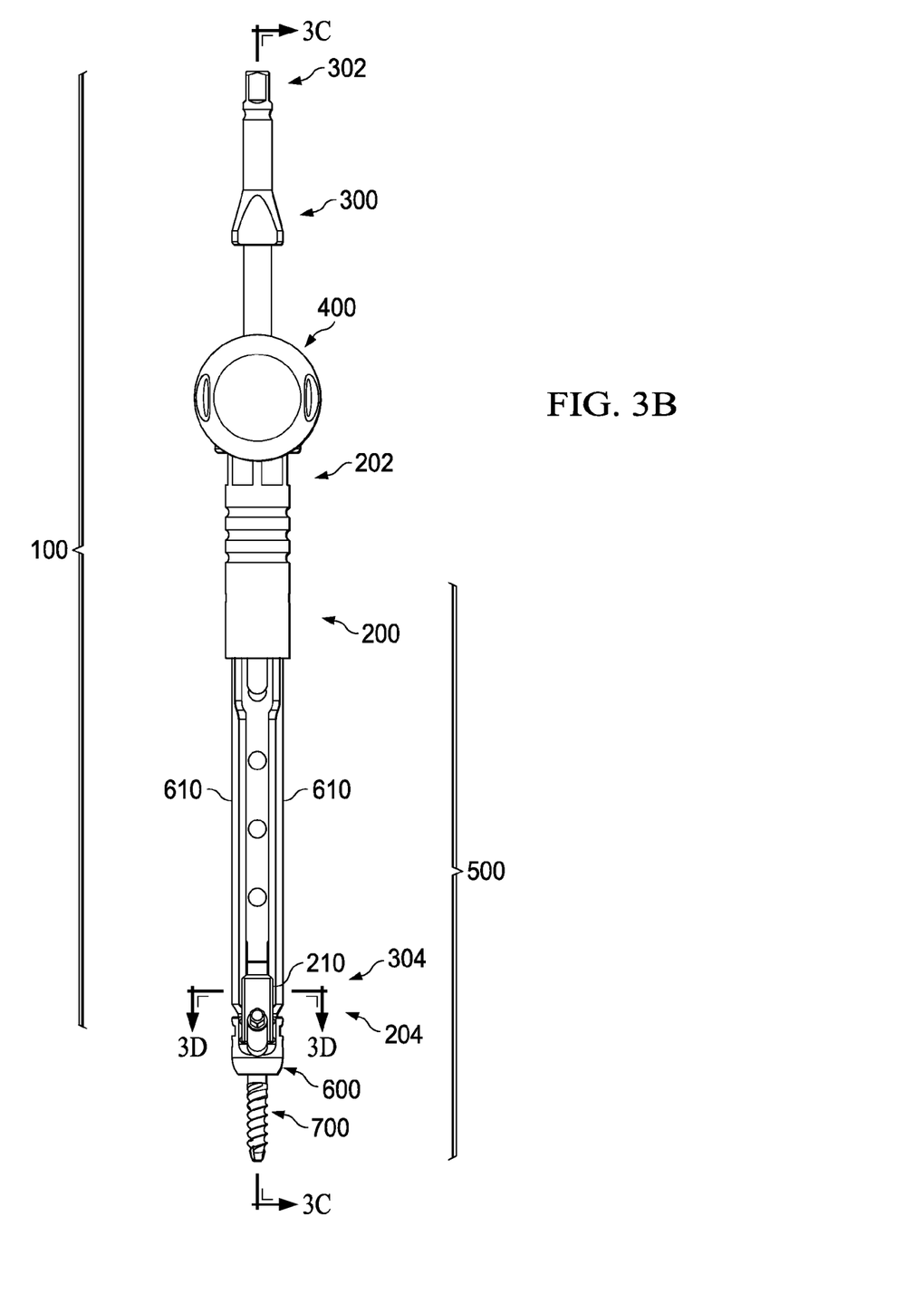
FIG. 3B illustrates another cross-sectional profile view of a counter-torque wrench system according to one embodiment of the present disclosure.

FIG. 3A and FIG. 3B illustrate cross-sectional profile views of the counter-torque wrench system 100 of FIGS. 1, 2A, and 2B, according to one embodiment of the present disclosure. More specifically, FIG. 3A and FIG. 3B illustrate the counter-torque wrench system 100 fitted into the bone screw system 500. FIG. 3A and FIG. 3B, by way of example, may depict the same counter-torque wrench system 100 and the bone screw system 500 rotated 90 degrees about an axis defined from the proximal end 202 to the distal end 204 of the counter-torque wrench 200 (as shown in FIGS. 1, 2A, and 2B).

As shown in FIG. 3A and FIG. 3B, the counter-torque wrench 200 may be inserted into the tulip head 600 of the bone screw system 500. The set screw driver 300 may be inserted into the hollow channel 206 of the counter-torque wrench 200. The proximal end 202 of the counter-torque wrench 200 may be operable to removably engage with the counter-torque wrench handle 400.

In some embodiments, the counter-torque wrench system 100 may advantageously stabilize the bone screw system 500 while a set screw 900 is fastened. The counter-torque wrench 100 may be biased against the mounting rod 800, thereby preventing the mounting rod 800 from rotating. For example, the wings 210 may be operable to press down on or exert pressure on either side of the mounting rod 800 relative to the tulip head 600. A rotational orientation of the counter-torque wrench 200 may be maintained or otherwise secured via use of the counter-torque wrench handle 400. For example, a user (i.e., a surgeon) may hold the counter-torque wrench handle 400 that has been engaged with a proximal end 302 of the counter-torque wrench 300. Such use of the counter-torque wrench handle 400 may prevent the counter-torque wrench 200 from rotating or otherwise moving. Accordingly, the counter-torque wrench 200 may promote stability of the bone screw system 500 and advantageously prevent movement of the mounting rod 800, the tulip head 600, the bone screw 700, or other components of the bone screw system 500. Movement of said components may be restricted or prevented while the set screw 900 is being fastened into the saddle 620 (as shown in FIG. 1).

The set screw 900 may be fastened into the saddle 620 via use of the set screw driver 300. The set screw driver 300 may comprise the proximal end 302 and a distal end 304. The set screw driver 300 may be inserted into the hollow channel 206 of the counter-torque wrench 200, and may have a length greater than that of the counter-torque wrench 200. Thus, in an assembled counter-torque wrench system 100, the proximal end 302 of the set screw driver 300 may extend above the proximal end 202 of the counter-torque wrench 200. Thus, the proximal end 302 of the set screw driver 300 may be operable to receive the removable set screw driver handle 1000 thereon. The distal end 304 of the set screw driver 300 may comprise an engaging member 306. The engaging member 306 may be operable to mate with the set screw 900 (as shown in FIG. 3A). For example, the engaging member 306 may comprise a hex or crosshead design which may mate with a corresponding design on the set screw 900. The set screw driver 300 may be operable to freely rotate within the hollow channel 206 of the counter-torque wrench 200. Thus, while the counter-torque wrench 200 may bias against the mounting rod 800 to stabilize the bone screw system 500 and prevent it from rotating, the set screw driver 300 may rotate and thereby fasten the set screw 900 into the saddle 602 of the bone screw system 500.

Embodiments of the present disclosure may advantageously provide for a more minimally invasive counter-torque wrench system 100. In some embodiments, the body 208 of the counter-torque wrench 200 may be positioned entirely within the space as defined by or between the removable arms 610 (as shown in FIG. 3B) of the tulip head 600. Receiving the body 208 (as shown in FIG. 2A and FIG. 2B) of the counter-torque wrench 200 within the tulip head 600 of the bone screw system 500 may advantageously provide for a more minimally invasive counter-torque wrench system 100 or a more minimally invasive surgical setting. Allowing the body 208 to be received within the tulip head 600 prevents some components from extending beyond a space as defined by or between the removable arms 610 of the tulip head 600. Thus, fewer components may need to be positioned outside the tulip head 600 or, for example, around the removable arms 610 or the saddle 620. As such, an overall width of the counter-torque wrench system 100 may be minimized or substantially reduced. A reduced width of the counter-torque wrench system 100 may advantageously allow for a smaller incision to be made during surgery. A smaller incision may be more minimally invasive while still providing sufficient width for the counter-torque wrench system 100 to be fitted or inserted within a patient's body.

In some embodiments, the counter-torque wrench handle 400 may be removably engaged to the proximal end 202 of the counter-torque wrench 200. The counter-torque wrench handle 400 may advantageously allow a user (i.e., a surgeon) to restrict movement or rotation of the counter-torque wrench 200. In some embodiments, the proximal end 202 of the counter-torque wrench 200 may comprise a polygonal cross section. An engagement portion 402 of the counter-torque wrench handle 400 may comprise a corresponding polygonal cavity or recess. For example, as shown in FIG. 1, the proximal end 202 of the counter-torque wrench 200 may comprise a hexagonal cross-section. Correspondingly, the engagement portion 402 of the counter-torque wrench handle 400 may comprise a hexagonal cavity or recess. A cavity or recess of the engagement portion 402 of the counter-torque wrench handle 400 may or may not extend through each end of the engagement portion 402. The hexagonal cross-section of the proximal end 202 of the counter-torque wrench 200 is merely one embodiment of the proximal end 202. One of ordinary skill in the art would appreciate that various polygonal shapes may be appropriate to allow for a secure engagement of the proximal end 202 of the counter-torque wrench 200 with the engagement portion 402 of the counter-torque wrench handle 400. Other appropriate geometries may include a triangle, rectangle, pentagon, heptagon, octagon, star, or cross.

The counter-torque wrench handle 400 may removably engage with the proximal end 202 of the counter-torque wrench 200. Removably engaging the counter-torque wrench handle 400 may comprise sliding the cavity of the engagement portion 402 over a corresponding polygonal cross-section of the proximal end 202 of the counter-torque wrench 200. Removal or release of the counter-torque wrench handle 400 may then comprise sliding the engagement portion 402 of the counter-torque wrench handle 400 off of the proximal end 202 of the counter-torque wrench 200.

When engaged with the counter-torque wrench 200, the counter-torque wrench handle 400 may restrict movement or rotation of the counter-torque wrench 200. One of ordinary skill in the art would appreciate that other mechanisms may be used to restrict movement or rotation of the counter-torque wrench 200 such that the counter-torque wrench 200 may stabilize the bone screw system 500 while the set screw driver 300 fastens the set screw 900. Such alternative mechanisms may be used in place of the counter-torque wrench handle 400 without departing from the present disclosure.

Figure 3C:
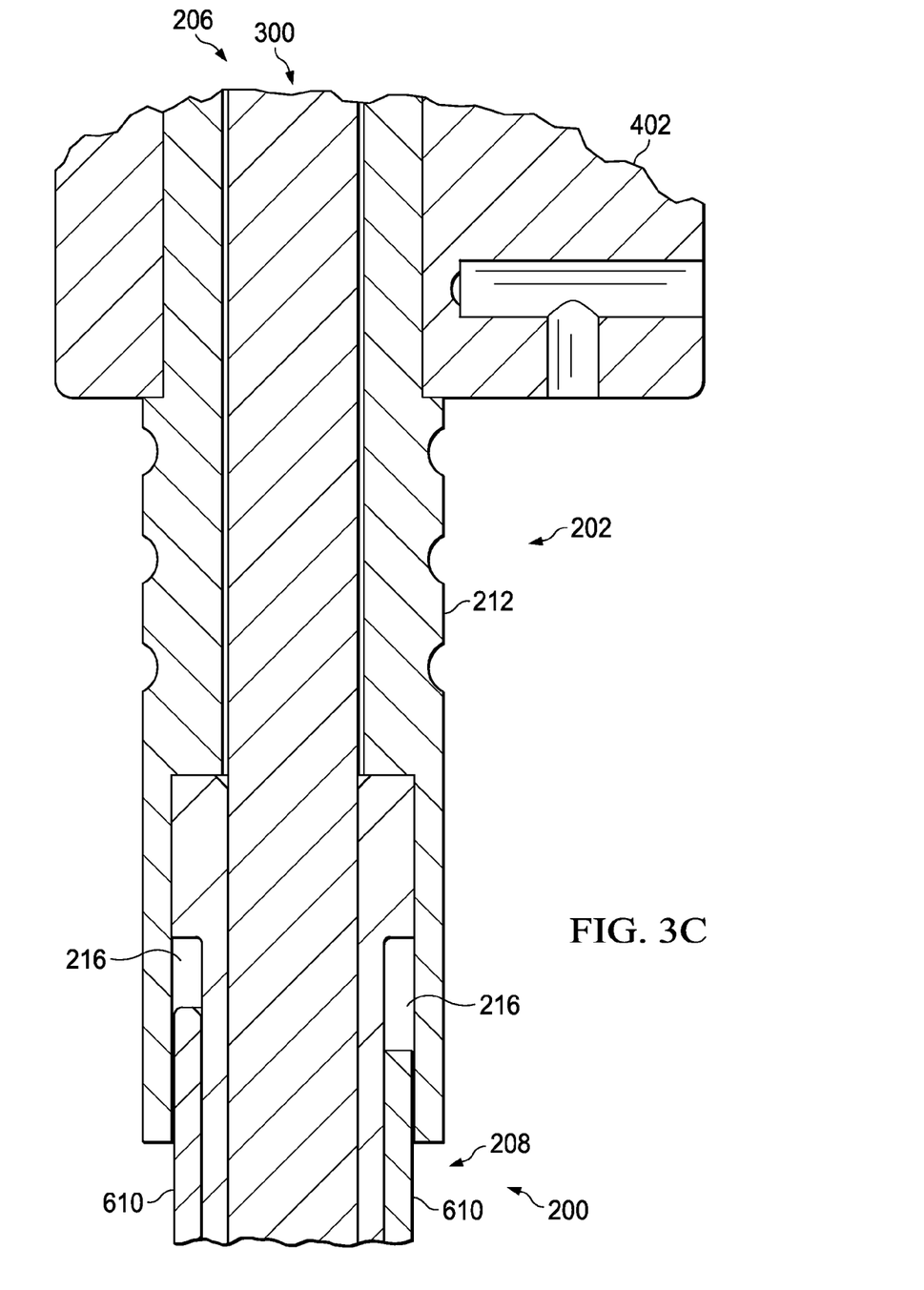
FIG. 3C illustrates a cross-sectional view of a proximal end of a counter-torque wrench system according to one embodiment of the present disclosure.

FIG. 3C illustrates a cross-sectional close-up view of the proximal end 202 of the counter-torque wrench 200 of FIGS. 1, 3A, and 3B, according to one embodiment of the present disclosure. More specifically, FIG. 3C depicts a close-up view of the proximal end 202 of the counter-torque wrench 200 shown in FIG. 3A and FIG. 3B. As shown in FIG. 3C, the proximal end 202 of the counter-torque wrench 200 may comprise the annular protrusion 212. The annular protrusion 212 may comprise a section with a greater diameter than the body 208 of the counter-torque wrench 200. The greater diameter of the annular protrusion 212 may advantageously allow for greater ease in manipulation of the counter-torque wrench 200.

In some embodiments, at least one slot 216 may be disposed at a distal end of the annular protrusion 212. As shown in FIG. 3C, the annular protrusion 212 may comprise two slots 216 at the distal end. The two slots 216 may have a width equal to or greater than a width of the removable arm 610 of the tulip head 600 (as shown in FIG. 1). Slots 216 may be operable to receive at least a distal portion of the removable arms 610 of the tulip head 600. Receiving at least a portion of the removable arm 610 in the slot 216 may advantageously secure a position of the removable arm 610 and prevent undesired splaying or breakage of the removable arm 610. The slots 216 disposed at the distal end of the annular protrusion 212 may be operable as an anti-splay sleeve.

Figure 3D:
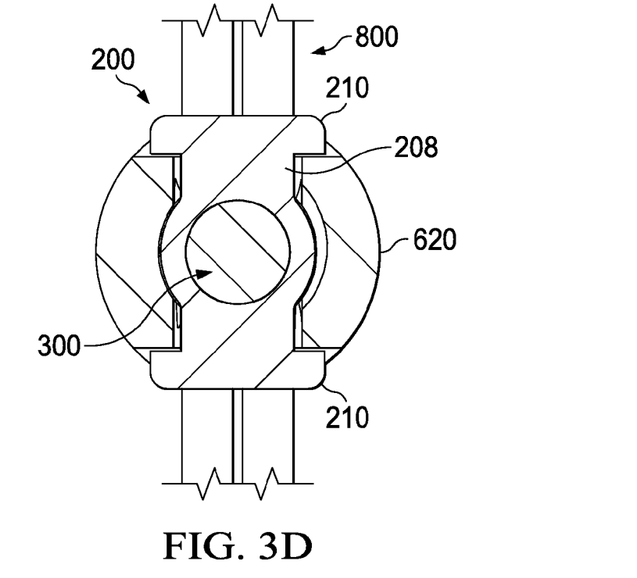
FIG. 3D illustrates a cross-sectional view of a distal end of a counter-torque wrench system according to one embodiment of the present disclosure.

FIG. 3D illustrates a cross-sectional view of the distal end 204 of the counter-torque wrench system 100 of FIGS. 1, 3A, 3B, and 3C, according to one embodiment of the present disclosure. FIG. 3D illustrates a top-down cross-sectional view of the distal end 204 of the counter-torque wrench 200 engaged with the bone screw system 500. As shown in FIG. 3D, the body 208 of the counter-torque wrench 200 may be inserted and may fit within the saddle 620 in the bone screw system 500 (as shown in FIG. 1). The counter-torque wrench 200 may be disposed above the mounting rod 800. As shown in FIG. 3D, the two wings 210 may be disposed outside of the tulip head 600 while the body 208 remains substantially entirely within the tulip head 600.

Figure 3E:
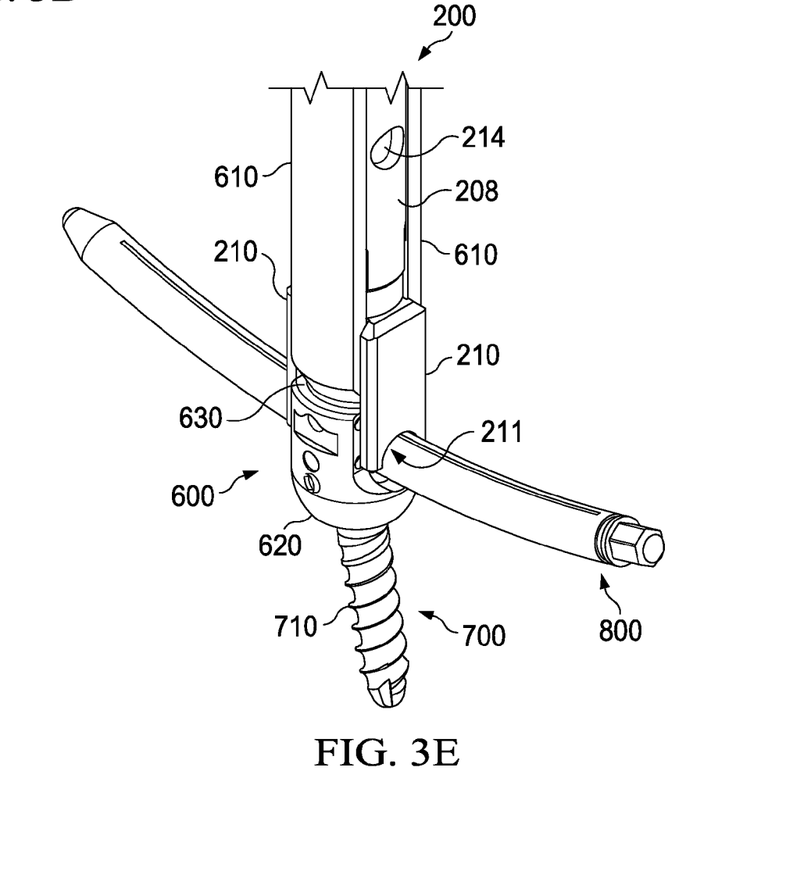
FIG. 3E illustrates a close-up perspective view of a distal end of a counter-torque wrench system according to one embodiment of the present disclosure.

FIG. 3E illustrates a close-up perspective view of the distal end 204 (as shown in FIG. 1) of the counter-torque wrench system 100 of FIGS. 1, 3A, 3B, 3C, and 3D, according to one embodiment of the present disclosure. As shown in FIG. 3E, each wing 210 of the counter-torque wrench 200 may be attached to or extend from the body 208 of the counter-torque wrench 200. Each wing 210 may be attached to the body 208 via a narrowed region or a neck region at the distal end 204 of the counter-torque wrench 200.

As shown in FIG. 3E, each of the at least one wing 210 may comprise a rectangular panel-like geometry comprising the curved surface 211 at a distal end of the wing 210. The curved surface 211 may correspond with a curvature of the cylindrical mounting rod 800. The curved surface 211 may contour against a curvature of the cylindrical mounting rod 800 and thereby allow the wings 210 to bias against the cylindrical mounting rod 800. The biasing of wings 210 against the mounting rod 800 may advantageously promote stability of the bone screw system 500 while the set screw 900 (as shown in FIG. 3A) is being fastened into the saddle 620.

As shown in FIGS. 2A and 2B, in some embodiments, the counter-torque wrench 200 may comprise the plurality of indentations 214. The plurality of indentations 214 may be disposed along an axis as defined from the proximal end 202 of the counter-torque wrench 200 to the distal end 204 of the counter-torque wrench 200. FIGS. 2A and 2B depict illustrative embodiments comprising four indentations 214 along an axis. As shown in FIGS. 2A and 2B, the indentations 214 may be circular in geometry. Other geometries such as ovals or polygons may be used without departing from the present disclosure.

The indentations 214 may form recesses or cavities on a wall of the body 208 of the counter-torque wrench 200. The indentations 214 may or may not extend all the way through the wall of the body 208 of the counter-torque wrench 200. In some embodiments, the indentations 214 may extend all the way through the wall of the body 208, thereby leaving the hollow channel 206 exposed or visible. As shown in FIGS. 1, 3B, and 3E, the indentations 214 that extend all the way through the wall of the body 208 may allow the set screw driver 300 to be visible at the indentations 214 when inserted into the hollow channel 206.

The indentations 214 may be operable to engage with a compression/distraction tool. A compression tool, such as pliers, may be used to manipulate the counter-torque wrench system 100. Manipulation of the counter-torque wrench system 100 may include manipulating or otherwise repositioning the counter-torque wrench 200 or the set screw driver 300 (as shown in FIG. 1). Tips or manipulating ends of the compression/distraction tool may engage with a recess or cavity formed by the indentations 214. As such, the indentations 214 advantageously allow for greater ease in the manipulation or repositioning of components in the counter-torque wrench system 100.

In some embodiments, the indentations 214 may align in a co-linear fashion with the wings 210. Such arrangement may allow the indentations 214 to be exposed even when counter-torque wrench 200 is inserted into the tulip head 600. While portions of the body 208 of the counter-torque wrench 200 may be concealed by the removable arms 610, the indentations 214 may still be exposed and accessible for manipulation by compression/distraction tools.

As seen in FIG. 3E, the removable arms 610, which may extend away from the patient, or distally, from the saddle 620 and may be hingedly connected to the saddle 620. For example, a connection between the saddle 620 and the removable arm 610 may comprise a thinner thickness of material at a crease 630. Thus, the removable arms 610 may be removed, splayed, or otherwise snapped off from the saddle 620. Removal of the removable arms 610 from the saddle 620 may be desirable after the bone screw system 500 has been securely fitted in a patient. However, removal of the removable arms 610 from the saddle 620 may be undesired prior to secure fitting of the bone screw system 500 (as seen in FIG. 1) or secure fastening of the set screw 900 (as seen in FIG. 3A) within the saddle 620.

Figure 4:
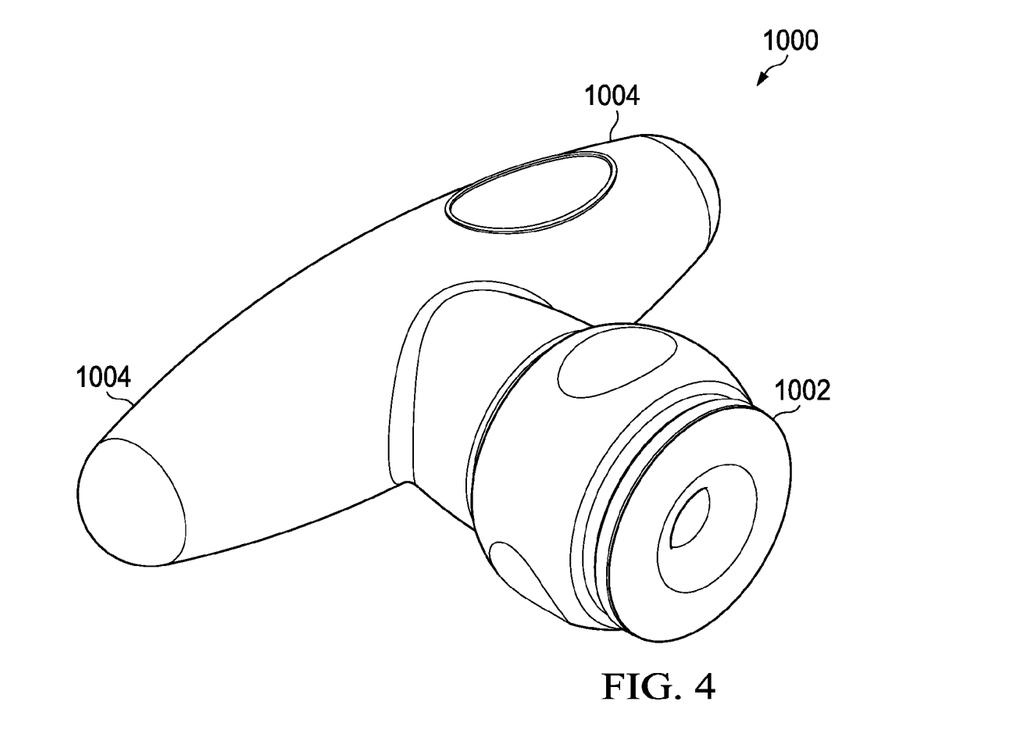
FIG. 4 illustrates a removable set screw driver handle of a counter-torque wrench system according to one embodiment of the present disclosure.

FIG. 4 illustrates the removable set screw driver handle 1000, and more specifically, a T-handle, of the counter-torque wrench system 100 of FIG. 1, according to one embodiment of the present disclosure. As shown in FIG. 4, the T-handle 1000 may comprise the engagement portion 1002. The engagement portion 1002 may comprise a recess that may correspond with the proximal end 302 of the set screw driver 300 (as shown in FIG. 3A). In some embodiments, the recess may comprise a hexagonal design. Such a hexagonal design may allow a protruding feature with a corresponding hexagonal design to mate with the recess in the T-handle.

As shown in FIG. 4, the T-handle 1000 may comprise two elongated counter-torque wrench handle ends 1004. One of ordinary skill in the art would appreciate that the number of elongated counter-torque wrench handle ends 1004 may by altered without departing from the present disclosure.

Figure 5:
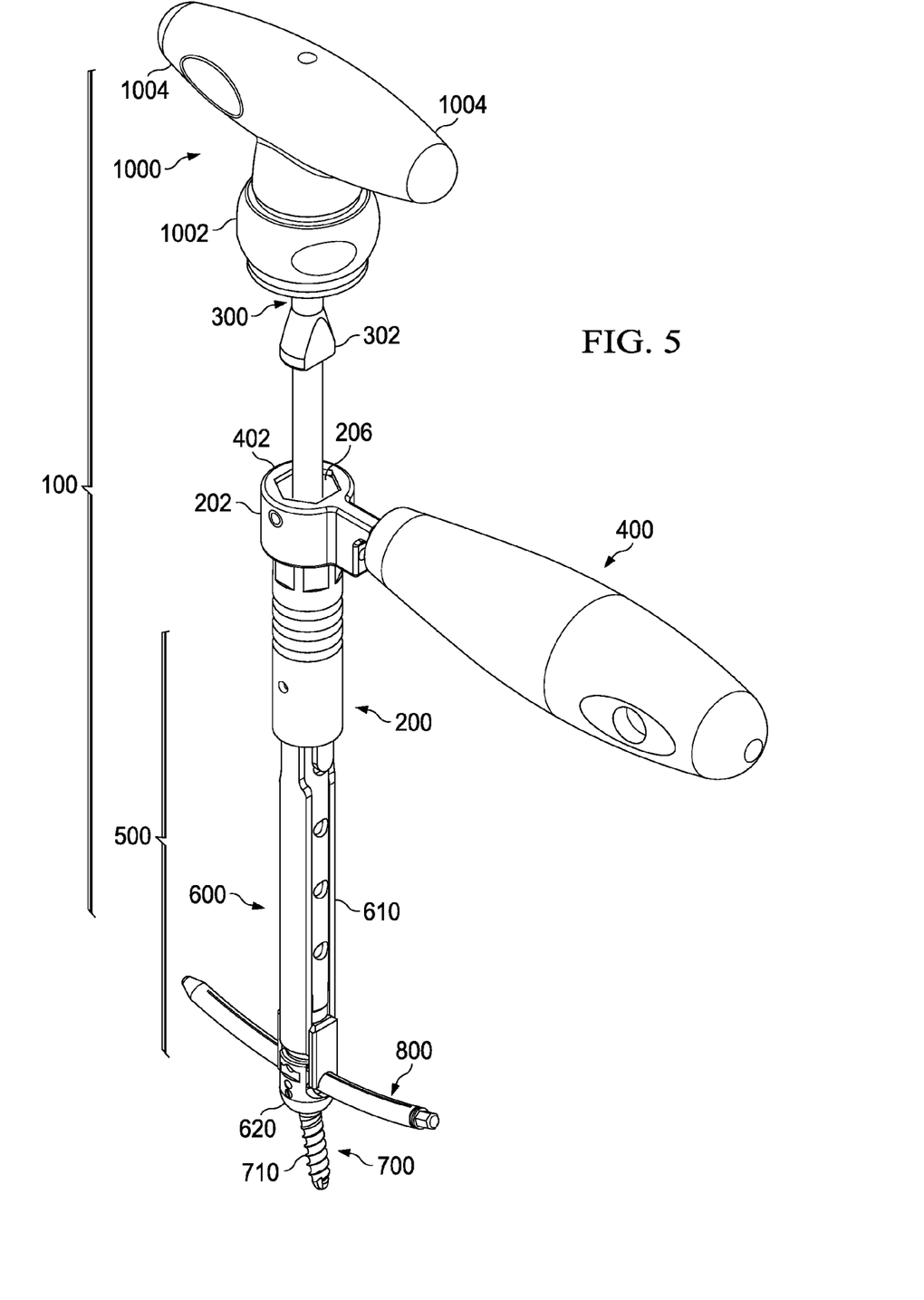
FIG. 5 illustrates a perspective view of a counter-torque wrench system according to one embodiment of the present disclosure.

FIG. 5 illustrates a perspective view of the counter-torque wrench system 100 of FIG. 1, according to one embodiment of the present disclosure. More specifically, the removable set screw driver handle 1000 may be engaged with the proximal end 302 of the set screw driver 300. Such engagement may advantageously allow for greater ease in rotating and securing the set screw driver 300. Engagement between the engagement portion 1002 of the T-handle 1000 and the proximal end 302 of the set screw driver 300 may comprise inserting the proximal end 302 into a recess in the engagement portion 1002. For example, as shown in FIG. 1, the set screw driver 300 may comprise a polygonal design at the proximal end 302. The polygonal design may allow for the proximal end 302 to be securely received within the engagement portion 1002 without risk of unintended rotation or unintended movement. In some embodiments, the polygonal design may be a hexagonal design. The polygonal design shown in FIG. 1 is illustrated by way of example only. One of ordinary skill in the art would appreciate that other polygonal structures or designs may be used without departing from the present disclosure.

Engagement between the engagement portion 1002 of the T-handle 1000 and the proximal end 302 of the set screw driver 300 may be facilitated by various features. For example, in some embodiments, there may be a ¼" square quick connect design on the T-handle 1000. Other connecting features or mechanisms may include an AO, Hudson, or Trinkle type quick connect. One of ordinary skill in the art would appreciate that such mechanisms are given by way of example only and that other connecting features or mechanisms may be used without departing from the present disclosure.

Use of the counter-torque wrench handle 1000 may allow a user (i.e., a surgeon) to rotate the set screw driver 300 within the hollow channel 206 of the counter-torque wrench 200 and thereby fasten the set screw 900 at the distal end 304 of the set screw driver 300. The counter-torque wrench handle 1000 may be turned or rotated by moving one of the at least one elongated counter-torque wrench handle ends 1004. The T-handle 1000 is described herein merely by way of example. One of ordinary skill in the art would appreciate that that other removable set screw driver handles 1000 may be used to provide for rotation of the set screw driver 300 and/or promote fastening of the set screw 900 at the distal end 304 of the set screw driver 300. Such alternative removable set screw driver handles 1000 may be used in place of the T-handle 1000 without departing from the present disclosure.

In some embodiments, the engaging member 306, disposed at the distal end 304, may be operable to mate with the set screw 900. The engaging member 306 may comprise a hex, crosshead, or any other protruding or receding feature. A top surface or proximal surface of the set screw 900 may comprise a corresponding hex, crosshead, or other protruding or receding feature. For example, the engaging member 306 comprising a protruding crosshead feature may be operable to mate with the set screw 900 comprising a corresponding receding crosshead feature on its proximal surface. The engaging member 306 mated with the set screw 900 may be operable to turn the set screw 900 upon rotation of the set screw driver 300. Such rotation may be facilitated by the removable set screw driver handle 1000 engaged at the proximal end 302 of the set screw driver 300. In some embodiments, fastening of the set screw 900 may be facilitated by clockwise rotations of the set screw 900 into the saddle 620.

The set screw 900 may comprise external threads operable to be fastened against or in corresponding threads of the saddle 620 of the tulip head 600 at a proximal region or top region of the saddle 620. One of ordinary skill in the art would appreciate that different types of threads may be used in the bone screw system 500. Different tulip heads 600 and set screws 900 may comprise different threads. For example, threads may vary in size, pitch, and/or angle. Matching or corresponding threads may be selected for particular embodiments without departing from the present disclosure.

In operation the bone screw system 500 may be provided. Providing the bone screw system 500 may comprise seating the bone screw 700 within the saddle 620. The bone screw 700 may then be fastened via the bone connection element 710 to a bone of a patient. The bone connection element 710 may be a screw-like structure comprising external threads. In some embodiments, the bone screw 700 may be fastened to a pedicle region of a patient's spine.

Once fastened, the mounting rod 800 may be disposed in the saddle 620. Disposing the mounting rod 800 in the saddle 620 may comprise lowering the mounting rod 800 through a channel between the removable arms 610 of the tulip head 600. The mounting rod 800 may be lowered through the channel until it sits within the saddle 620 of the tulip head 600. In some surgical settings, the mounting rod 800 may be disposed along multiple saddles 620 of multiple tulip heads 600. Such arrangement may advantageously allow for the mounting rod 800 to stabilize movement between multiple bone screw systems 500.

After the mounting rod 800 is disposed within the saddle 620, the set screw 900 may be disposed within the saddle 620 by sliding the set screw 900 down the channel between the removable arms 610 of the tulip head 600. In some embodiments, the set screw 900 may have a diameter substantially equal to or less than a diameter formed by the spacing between the removable arms 610. The set screw 900 may be lowered between the removable arms 610 and rest within the saddle 620.

According to various embodiments of the present disclosure, methods of fastening the set screw 900 within the bone screw system 500 may comprise inserting the counter-torque wench 200 into the tulip head 600. The counter-torque wrench 200 may comprise any of the features and/or embodiments in the aforementioned descriptions. For example, the counter-torque wrench 200 may comprise the proximal end 202, the distal end 204, the body 208, the at least one wing 210, and the hollow channel 206. The counter-torque wrench 200 may be lowered into the tulip head 600. Methods may further comprise disposing an at least one wing 210 outside of the tulip head 600. Methods may further comprise biasing each of the curved surfaces 211 of the wings 210 against the corresponding curvature of the mounting rod 800.

In some embodiments, methods may further comprise securing at least a proximal portion of the removable arm 610 of the tulip head 600 within the slot 216 disposed at the distal end of the annular protrusion 212. Such securing may advantageously prevent undesired or premature splaying or breakage of the removable arms 610 from the saddle 620 of the tulip head 600. Such securing may also advantageously provide for additional compressive forces upon the bone screw system 500.

Methods of fastening the set screw 900 to the bone screw system 500 may further comprise inserting the set screw driver 300 into the hollow channel 206 of the counter-torque wrench 200. The set screw driver 300 may be inserted into the hollow channel 206 before or after the counter-torque wrench 200 is inserted into the tulip head 600. Methods may further comprise mating the engaging member 306 at the distal end 304 of the set screw driver 300 to the set screw 900 disposed within the saddle 620.

The counter-torque wrench handle 400 may be engaged with the proximal portion 202 of the counter-torque wrench 200, and the removable set screw driver handle 1000 may be engaged to the proximal end 302 of the set screw driver 300. Next, the user (i.e., a surgeon) may hold the counter-torque wrench handle 400 in place with one hand to prevent the counter-torque wrench 200 from moving or rotating. The user may also press down on the counter-torque wrench handle 400 to exert a compressive force on the counter-torque wrench 200 which may create additional pressure or stability on the bone screw system 500. The user may then use his or her other hand to rotate the removable set screw driver handle 1000 in order to fasten the set screw 900 engaged to the distal end 304 of the set screw driver 300. For example, a user may turn the T-handle 1000 engaged at the proximal end 302 of the set screw driver 300. Such turning or rotation may be clockwise or counter-clockwise depending on the threading orientation of the set screw 900 and the corresponding saddle 620. Thus, the set screw 900 may be rotated with the set screw driver 300 and may be mated against the rod 800.

Methods of the present disclosure may further comprise disassembling the counter-torque wrench system 100. Disassembly of the counter-torque wrench system 100 may be performed after the set screw 900 has been fastened to the bone screw system 500. Methods of disassembly may comprise removing the counter-torque wrench handle 400, removing the set screw driver 300, and removing the counter-torque wrench 200. The counter-torque wrench handle 400 may be removed along with or independent of the counter-torque wrench 200. Similarly, the set screw driver 300 may be removed along with or independent of the counter-torque wrench 200.

After the counter-torque wrench system 100 has been removed from the bone screw system 500, disassembly may further comprise removing the removable arms 610 from the bone screw system 500. Removable arms 610, which may extend from the saddle 620, may be hingedly connected to the saddle 620. For example, a connection between the saddle 620 and the removable arm 610 may comprise a thinner material or a crease 630 thereon. Such crease 630 may be shown in FIG. 3E. Removal of the removable arms 610 may comprise folding, splaying, or otherwise snapping off the removable arms 610 from the saddle 620 at the crease 630. One of ordinary skill in the art would appreciate that other methods of severing the removable arms 610 from the bone screw system 500 may be used without departing from the present disclosure. Removal of the removable arms 610 may leave only the saddle 620, the set screw 900, the bone screw 700, the mounting rod 800, and other components within the saddle 620 as part of the bone screw system 500.

In any of the embodiments of the present disclosure, the materials may be chosen and may be varied to fit a number of functional and design considerations. In some embodiments, the bone screw 700, the tulip head 600, the mounting rod 800, the counter-torque wrench 200, and the set screw driver 300 may be made of materials such as titanium, titanium alloys (ex. Ti-6Al-4V), aluminum, stainless steel, or cobalt chrome alloy, polymer (ex. Radel, Ultem, or PEEK) or carbon filled polymer.

One of ordinary skill in the art would appreciate that other implantable metallic or polymeric materials may be used without departing from the present disclosure. Furthermore, a material for each component may be independently selected and a material of each component may vary from one another without departing from the present disclosure.

The present disclosure provides for systems and methods of counter-torque wrenches and counter-torque wrench systems. In various embodiments, differing dimensions of the various components may be employed as necessary or desirable for particular patients or surgical settings.

According to some embodiments, the counter-torque wrench 200 may have a length of approximately 150 mm to approximately 200 mm. In some embodiments, the counter-torque wrench 200 may have a length of approximately 170 mm.

The body 208 of the counter-torque wrench 200 may have a diameter of approximately 8 mm to approximately 12 mm. In some embodiments, the body 208 may have a diameter of approximately 10 mm.

The annular protrusion 212 of the counter-torque wrench 200 may have a diameter of approximately 12 mm to approximately 20 mm. In some embodiments, the annular protrusion 212 may have a diameter of approximately 17 mm. The slots 216 disposed at a distal end of the annular protrusion 212 may have a depth of approximately 8 mm to approximately 16 mm and a width of approximately 1 mm to approximately 3 mm. A width of a slot 216 may be equal to or greater than to a width of the removable arm 610. A slot 216 width equal to the removable arm 610 width may provide for a more secure engagement of the two components.

The hollow channel 206 of the counter-torque wrench 200 may have a diameter of approximately 6 mm to approximately 11 mm. In some embodiments, the hollow channel 206 may have a diameter of approximately 8 mm.

The distal end 204 of the counter-torque wrench 200 may have a diameter of approximately 12 mm to approximately 15 mm. In some embodiments, the distal end 204 of the counter-torque wrench 200 may have a diameter of approximately 13.5 mm. A measurement of a width of the distal end 204 may comprise the distance from one wing 210 to another wing 210.

The wings 210 of the counter-torque wrench 200 may have a height of approximately 17 mm to approximately 21 mm. The wing 210 of the counter-torque wrench 200 may have a width of approximately 7 mm to approximately 10 mm. A width may correspond to or be substantially similar to a width of the saddle 620. The width may be greater than a diameter of the mounting rod 800 such that the curved surface 211 of the wing 210 may bias on a curvature of the mounting rod 800. The wing 210 of the counter-torque wrench 200 may have a thickness of approximately 1 mm to approximately 3 mm. In some embodiments, the thickness may be approximately 2 mm. Providing for thicker wings 210 may advantageously provide for a more sturdy or durable distal end 204 of the counter-torque wrench 200. A thicker wing 210 may advantageously provide for greater ease in creating a compressive force upon the mounting rod 800. Providing for thinner wings 210 may advantageously provide for a more compact or more minimally invasive counter-torque wrench systems 100. Thinner wings 210 may reduce the overall width or diameter of the counter-torque wrench 200 and the counter-torque wrench system 100. Thus, thinner wings 210 may advantageously allow for small incisions to be made during surgery, as less space would be needed to allow for the counter-torque wrench 200 to be inserted into a patient's body.

According to some embodiments, the set screw driver 300 may have a length of approximately 200 mm to approximately 240 mm. In some embodiments, the set screw drive 300 may have a length of approximately 220 mm. The set screw driver 300 may have a length greater than a length of the counter-torque wrench 200. A great length may allow the proximal end 320 of the set screw drive 300 to be manipulated by, for example, the removable set screw driver handle 1000.

The set screw driver 300 may have a diameter of approximately 6 mm to approximately 9 mm. In some embodiments, the set screw drive 300 may have a diameter of approximately 7.5 mm. The set screw driver 300 may have a diameter substantially similar to or less than a diameter of the hollow channel 206 in the counter-torque wrench 200. The set screw driver 300 with a diameter substantially similar to a diameter of the hollow channel 206 may provide for a more secure fit but result in greater friction or resistance upon rotation of the set screw driver 300 within the hollow channel 206. The set screw driver 300 with a diameter less than a diameter of the hollow channel 306 may provide for greater ease in rotation of the set screw driver 300 but result in a degree of instability of the set screw driver 300 within the hollow channel 206.

As will be understood by those skilled in the art who have the benefit of the instant disclosure, other equivalent or alternative compositions, devices, methods, and systems for counter-torque wrenches may be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of wings, indentations, and removable arms may be varied. In some embodiments, set screws, set screw drivers, and counter-torque wrench handles may be interchangeable. For example, interchangeability may allow set screw drivers to be custom adjusted (e.g., by length or diameter). In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/−about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for counter-torque wrenches may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A counter-torque wrench system operable for connecting to a bone screw system including a tulip head with at least one removable arm and a saddle, and a mounting rod with a curvature, the counter-torque wrench system comprising:
    a counter-torque wrench comprising:
        a proximal end;
        a distal end;
        a body;
        at least one wing comprising a curved surface at a distal end of the at least one wing, wherein the at least one wing is disposed at the distal end of the counter-torque wrench, and wherein an outer surface of the at least one wing is substantially within an outer circumference of the saddle; and
        a hollow channel extending from the proximal end of the counter-torque wrench to the distal end of the counter-torque wrench; and
    a set screw driver comprising:
        a proximal end; and
        a distal end, wherein the distal end of the set screw driver comprises an engaging member;
    wherein the body of the counter-torque wrench is operable to be received within the at least one removable arm of the tulip head of the bone screw system;
    wherein the curved surface of each of the at least one wing is operable to contour against the curvature of the mounting rod when the counter-torque wrench reduces the mounting rod into the saddle, and
    wherein the set screw driver is operable to be received within the hollow channel of the counter-torque wrench.

2. The counter-torque wrench system according to claim 1, wherein the proximal end of the counter-torque wrench comprises an annular protrusion; and wherein the annular protrusion comprises at least one slot disposed at a distal end of the annular protrusion; and wherein the at least one slot is operable to receive at least a distal portion of a removable arm of the tulip head.

3. The counter-torque wrench system according to claim 1, wherein the proximal end of the counter-torque wrench is operable to removably engage with a counter-torque wrench handle.

4. The counter-torque wrench system according to claim 1, wherein the counter-torque wrench comprises two wings.

5. The counter-torque wrench system according to claim 1, wherein the at least one wing is disposed outside the tulip head of the bone screw system.

6. The counter-torque wrench system according to claim 1, wherein the body comprises a plurality of indentations disposed along an axis as defined from the proximal end of the counter-torque wrench to the distal end of the counter-torque wrench.

7. The counter-torque wrench system according to claim 6, wherein the plurality of indentations are operable to engage with a compression tool.

8. The counter-torque wrench system according to claim 1, wherein the set screw driver is operable to rotate within the hollow channel of the counter-torque wrench.

9. The counter-torque wrench system according to claim 1, wherein the engaging member is operable to mate with a set screw and to secure the set screw within the bone screw system.

10. The counter-torque wrench system according to claim 1, wherein the proximal end of the set screw driver is operable to engage with a T-handle.

* * * * *